United States Patent
O'Dell et al.

(10) Patent No.: US 7,348,428 B2
(45) Date of Patent: Mar. 25, 2008

(54) TRIARYLAMINE CONTAINING MONOMERS FOR OPTOELECTRONIC DEVICES

(75) Inventors: Richard O'Dell, Taufkirchen (DE); Carl Towns, Stansted (GB); Mary McKiernan, Cottenham (GB)

(73) Assignee: Cambridge Display Technology Limited, Cambridgeshire (GB)

( * ) Notice: Subject to any disclaimer, the term of this patent is extended or adjusted under 35 U.S.C. 154(b) by 597 days.

(21) Appl. No.: 10/493,637

(22) PCT Filed: Oct. 18, 2002

(86) PCT No.: PCT/GB02/04723

§ 371 (c)(1),
(2), (4) Date: Sep. 21, 2004

(87) PCT Pub. No.: WO03/035714

PCT Pub. Date: May 1, 2003

(65) Prior Publication Data

US 2005/0070710 A1    Mar. 31, 2005

(30) Foreign Application Priority Data

Oct. 25, 2001    (GB) ................. 0125620.5

(51) Int. Cl.
*C07F 5/02*    (2006.01)
(52) U.S. Cl. ............. 544/209; 546/13; 548/405; 558/298
(58) Field of Classification Search ........ 544/209; 546/13; 558/298
See application file for complete search history.

(56) References Cited

U.S. PATENT DOCUMENTS 5,523,555 A    6/1996 Friend et al. ......... 250/214 R
5,670,791 A    9/1997 Halls et al. ............ 257/40

FOREIGN PATENT DOCUMENTS

| GB | 2315594 | 2/1998 |
|---|---|---|
| WO | WO 90/13148 | 11/1990 |
| WO | WO 92/03490 | 3/1992 |
| WO | WO 96/16449 | 5/1996 |
| WO | WO 97/05184 | 2/1997 |
| WO | WO 97/42666 | 11/1997 |
| WO | WO 98/06773 | 2/1998 |
| WO | WO 99/09603 | 2/1999 |
| WO | WO 99/48160 | 9/1999 |
| WO | WO 99/49525 | 9/1999 |
| WO | WO 99/54385 | 10/1999 |
| WO | WO 00/53656 | 9/2000 |
| WO | WO 00/55927 | 9/2000 |
| WO | WO 01/44769 A1 | 6/2001 |
| WO | WO 01/49768 A2 | 7/2001 |
| WO | WO 01/49769 A1 | 7/2001 |
| WO | WO 01/66618 A1 | 9/2001 |

OTHER PUBLICATIONS

International Search Report in PCT/GB02/04723 dated Jan. 20, 2003.

*Primary Examiner*—Kamal A. Saeed
(74) *Attorney, Agent, or Firm*—Marshall, Gerstein & Borun LLP

(57) ABSTRACT

Monomers having the formula $X_1$—$Ar_1$-[triarylamine]—$Ar_2$-$X_2$ wherein the triarylamine unit comprises at least one nitrogen atom in the backbone of the monomer and at least three substituted or unsubstituted aryl or heteroaryl groups and wherein $X_1$ and $X_2$ are the same or different polymerizable groups and wherein $Ar_1$ and $Ar_2$ are the same or different substituted or unsubstituted aryl or heteroaryl groups. Polymers and copolymers comprising such monomers are also described. The polymers have particular application in organic optoelectronic devices such as organic electroluminescent devices and organic photovoltaic devices.

27 Claims, No Drawings

TRIARYLAMINE CONTAINING MONOMERS FOR OPTOELECTRONIC DEVICES

This is the U.S. national phase of International Application No. PCT/GB02/04723 filed Oct. 18, 2002, the entire disclosure of which is incorporated herein by reference.

BACKGROUND OF THE INVENTION

1. Field of the Invention

The invention relates to triarylamine based trimer monomers and to low band gap polymers and copolymers prepared therefrom and in particular to optoelectronic devices such as electroluminescent devices and photovoltaic devices comprising such polymers and copolymers.

2. Description of Related Technology

Semiconductive organic polymers have been known for several decades, during the past ten years they have seen increasing application in the field of electroluminescent devices, see for example WO90/13148. A typical electroluminescent device comprises an anode, a cathode and a layer of light-emitting material situated between the anode and the cathode, further layers may also be introduced to improve charge injection into the device or charge transport through the device. Semiconductive organic polymers may act as the light-emitting component or as charge transport or charge injecting components in electroluminescent devices. More recently semiconductive organic polymers have found application in photovoltaic devices, as disclosed in WO96/16449, and also as photoconductors and photodetectors.

The nature of the polymeric material used in electroluminescent devices is critical to the performance of the device, materials used include poly(phenylenevinylenes), as disclosed in WO90/13148, polyfluorenes, as disclosed in WO97/05184, poly(arylamines), as disclosed in WO98/06773. In particular copolymers and blends of polymers have been found to be useful in such devices, as disclosed in WO92/03490, WO99/54385, WO00/55927 and WO99/48160. Poly(arylamines) have been disclosed in which the aromatic groups may comprise heteroaromatic moieties such as triazine, see WO01/49769.

Recently there have been efforts to increase the range of available semiconductive polymers and, in particular, to provide polymers with lower band gaps, see WO01/49768. The band gap is the difference in energy levels between the highest occupied molecular orbital (HOMO) and the lowest unoccupied molecular orbital (LUMO). Low band gap materials emit light at longer wavelengths i.e. towards the red end of the visible region of the electromagnetic spectrum and are also promising candidates for polymeric photovoltaic devices. WO01/49768 discloses a range of low band gap polymers comprising heterocyclic moieties such as benzothiadiazole. Benzothiadiazole is a functional group characterised by its light-emitting and electron transporting properties.

SUMMARY OF THE INVENTION

The invention provides a range of low band gap polymers and copolymers which give efficient emission of light and have utility as hole-transporting components in optoelectronic devices. The invention provides a range of monomers which may be polymerised to provide low band gap polymers and copolymers, the invention further provides optoelectronic devices comprising the polymers and copolymers and methods for the polymerization of said monomers.

In a first embodiment the invention provides monomers having the formula

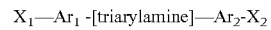

wherein the triarylamine unit comprises at least one nitrogen atom in the backbone of the monomer and at least three substituted or unsubstituted aryl or heteroaryl groups, said groups being the same or different, wherein $X_1$ and $X_2$ are the same or different polymerization groups, wherein $Ar_1$ and $Ar_2$ are the same or different substituted or unsubstituted aryl or heteroaryl groups.

For the purpose of the invention the term "the backbone of the monomer" is taken to mean that linear chain to which all other chains may be regarded as being pendant, i.e. that part of the monomer which will be situated in the backbone of the eventual polymer. The backbone is sometimes also referred to as the main chain.

In a more preferred embodiment groups $Ar_1$ and $Ar_2$ are heteroaromatic groups such as thiophene, pyrrole, furan or pyridine, thiophene is particularly preferred. Polymerizable groups $X_1$ and $X_2$ are preferably selected from the group comprising Cl, Br, 1, boronic acids, boronic esters or boranes. In a preferred embodiment polymerizable groups $X_1$ and $X_2$ are selected from the group comprising Br and boronic esters.

The groups $Ar_1$ and $Ar_2$ may be substituted with moieties selected from the group comprising aryl, alkyl, cycloalkyl and alkoxy.

The triarylamine group may comprise a heteroaryl group, this may be either in the chain of the monomer or pendant to the monomer, examples of heteroaryl groups are pyridine, and triazine. In a preferred embodiment the triarylamine comprises a triazine group. The triarylamine group comprises at least one nitrogen, in preferred embodiments the triarylamine group comprises one or two nitrogens.

Particularly preferred monomers are those having the structural formula

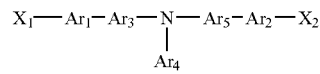

wherein $X_1$ and $X_2$ are the same or different polymerizable groups and wherein $Ar_1$, $Ar_2$, $Ar_3$, $Ar_4$ and $Ar_5$ are the same or different substituted or unsubstituted aryl or heteroaryl groups. Or those monomers having the structural formula

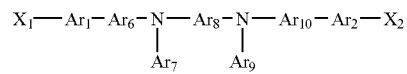

wherein $X_1$ and $X_2$ are the same or different polymerizable groups and wherein $Ar_1$, $Ar_2$, $Ar_6$, $Ar_7$, $Ar_8$, $Ar_9$, and $Ar_{10}$ are the same or different substituted or unsubstituted aryl or heteroaryl groups. Examples of groups $Ar_1$, $Ar_2$, $Ar_3$, $Ar_4$, $Ar_5$, $Ar_6$, $Ar_7$, $Ar_8$, $Ar_9$, and $Ar_{10}$ include such groups as phenylene, thiophene, pyrrole, furan, pyridine and biphenylene.

The aryl or heteroaryl groups $Ar_3$, $Ar_4$, $Ar_5$, $Ar_6$, $Ar_7$, $Ar_8$, $Ar_9$, and $Ar_{10}$ may be substituted with moieties selected from the group comprising alkyl, perfluoroalkyl, alkylaryl, arylalkyl, heteroaryl, aryl, alkoxy, aryloxy and thioalkyl. Preferred substituents are butyl and sec-butyl.

Particularly preferred monomers according to the invention include

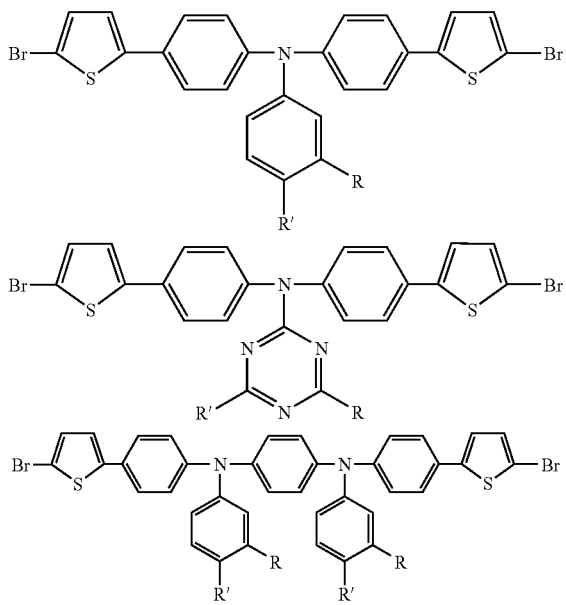

wherein R and R' are selected from the group consisting of alkyl, perfluoroalkyl, alkylaryl, arylalkyl, heteroaryl, aryl, alkoxy, aryloxy, and thioalkyl, preferably and R and R' are selected from the group consisting of butyl and sec-butyl.

The invention provides polymers obtainable by the polymerization of the monomers of the present invention. The invention also provides copolymers obtained by the polymerization of monomers of the present invention with suitable comonomers, preferred comonomers are those selected from the group comprising fluorenes, benzothiadiazoles, phenylenes, triarylamines, quinoxalines and stilbenes, preferably said comonomers are fluorenes, benzothiadiazoles, phenylenes or triarylamines.

In a further embodiment the invention provides an optoelectronic device comprising the polymers or copolymers of the invention. In preferred embodiments said optoelectronic device is an electroluminescent device or a photovoltaic device.

The invention provides a process for preparing the inventive polymers comprising polymerizing in a reaction mixture (a) an inventive monomer having at least two boron derivative functional groups selected from a boronic acid group, a boronic ester group and a borane group, and an inventive monomer having at least two reactive halide functional groups; or (b) an inventive monomer having one reactive halide functional group and one boron derivative functional group selected from a boronic acid group, a boronic ester group and a borane group, wherein the reaction mixture comprises a catalytic amount of a catalyst suitable for catalyzing the polymerization of the aromatic monomers, and a base in an amount sufficient to convert the boron derivative functional groups into $BX_3$-anionic groups, wherein X is independently selected from the group consisting of F and OH.

The invention provides a process for preparing the inventive copolymers which comprises polymerizing in a reaction mixture (a) an inventive monomer having at least two boron derivative functional groups selected from a boronic acid group, a boronic ester group and a borane group, and one or more comonomers having at least two reactive halide functional groups; or (b) an inventive monomer having at least two reactive halide functional groups, and one or more comonomers having at least two boron derivative functional groups selected from a boronic acid group, a boronic ester group and a borane group; or at least (c) an inventive monomer having one reactive halide functional group and one boron derivative functional group selected from a boronic acid group, a boronic ester group and a borane group and one or more comonomers having one reactive halide functional group and one boron derivative functional group selected from a boronic acid group, a boronic ester group and a borane group wherein the reaction mixture comprises a catalytic amount of a catalyst suitable for catalysing the polymerization of the aromatic monomers, and a base in an amount sufficient to convert the boron derivative functional groups into-$BX_3$-anionic groups, wherein X is independently selected from the group consisting of F and OH.

DETAILED DESCRIPTION OF THE INVENTION

Monomers according to the invention can be prepared by any suitable route known to those skilled in the art. A preferred route involves Ullmann condensation to afford the amine units and Stille coupling to connect the amine units to further aryl or heteroaryl groups. An example of a typical synthetic route is shown

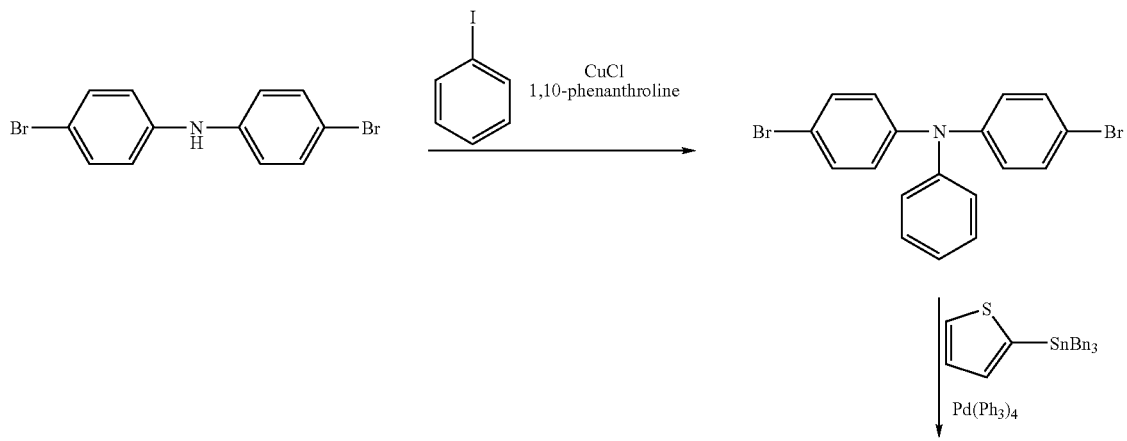

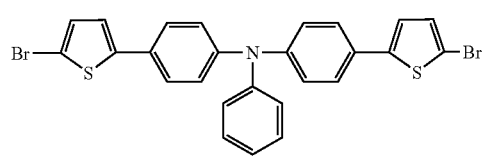

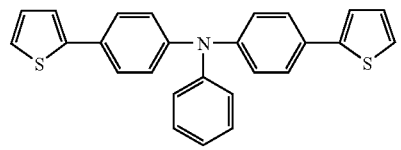

-continued

← BuLi, BrCF₂CF₂Br

In the above scheme a triarylamine is formed by Ullmann condensation of a diamine and an aromatic iodide, this condensation is generally carried in an inert solvent in the presence of a catalyst such as copper powder, cuprous oxide, cuprous chloride, cuprous bromide, cuprous iodide or cuprous sulfate, 1,10-phenanthroline is added to expedite the reaction. Stile coupling is a common method of coupling aromatic units to heteroaromatic units, in the above scheme the electrophile substituted triarylamine is reacted with an organotin reagent in the presence of a palladium catalyst. Modifications of both Ullmann condensation and Stille coupling are well known to those in the art.

Examples of monomers according to the invention include those having the following structural formulae

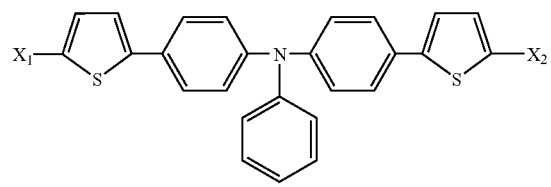

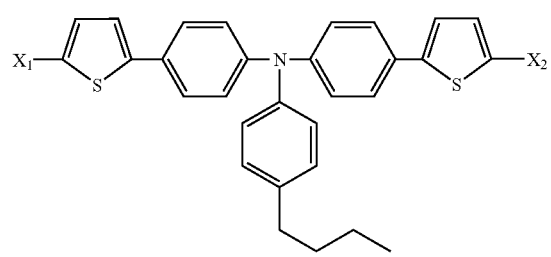

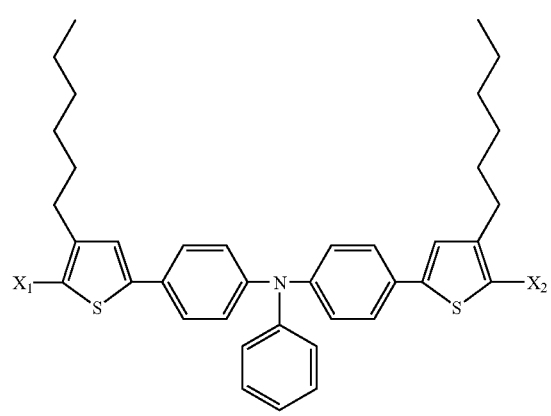

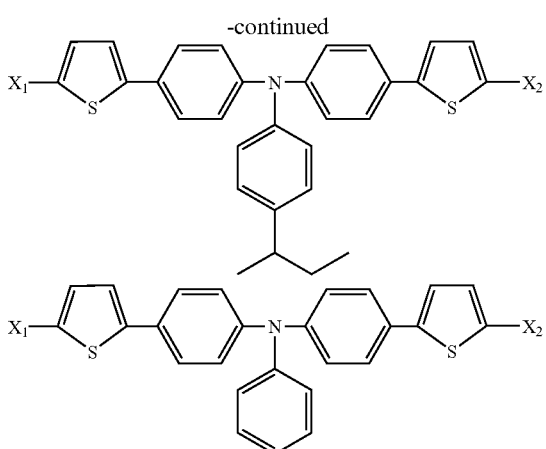

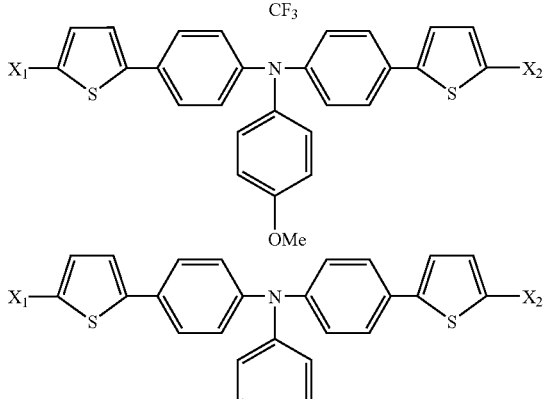

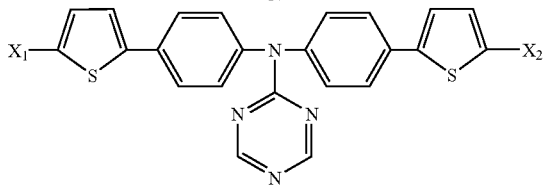

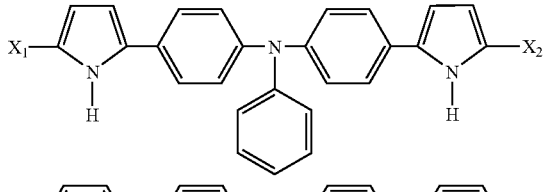

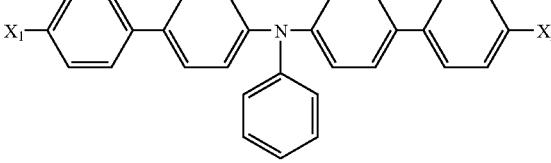

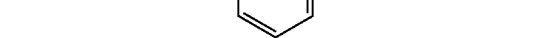

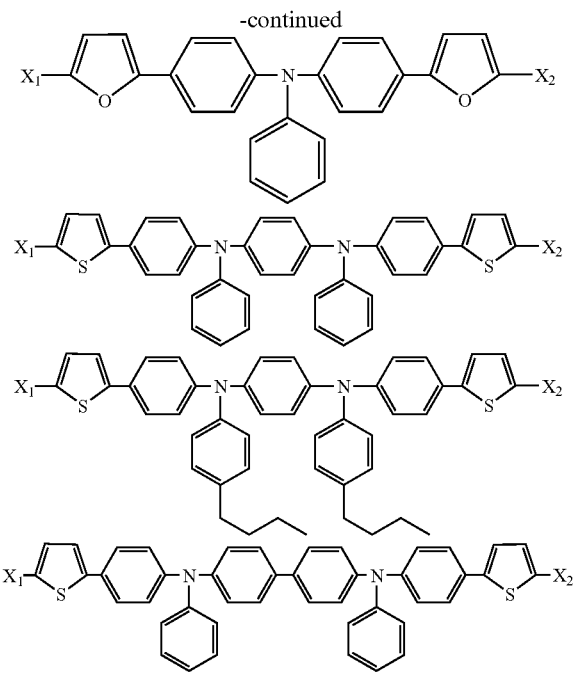

Polymers and copolymers according to the invention may be prepared by any suitable method known to those skilled in the art, such as Yamamoto or Suzuki coupling, Suzuki coupling is preferred. In the case of monomers with thiophene or pyrrole substituents polymers and copolymers may be prepared by electrochemical polymerization. Generally, in order to prepare a polymer by Suzuki coupling a suitably substituted monomer is polymerized in a solvent in the presence of a catalyst and a base. Suitable monomers are those comprising, for example, one polymerizable Br moiety and one polymerizable boronic ester moiety, alternatively the reaction mixture may comprise two monomers, one having, for example Br substituents and the other having, for example, boronic ester substituents. The catalyst is a palladium catalyst such as tetrakis(triphenylphosphine)palladium, suitable bases include alkali or alkaline earth carbonates and alkali or alkaline earth bicarbonates or organic bases such as those disclosed in WO 00/53656. The solvent is preferably one in which the polymer is soluble, for example suitable solvents include anisole, benzene, ethylbenzene, mesitylene, xylene and toluene. A typical reaction scheme for Suzuki polymerization is shown below.

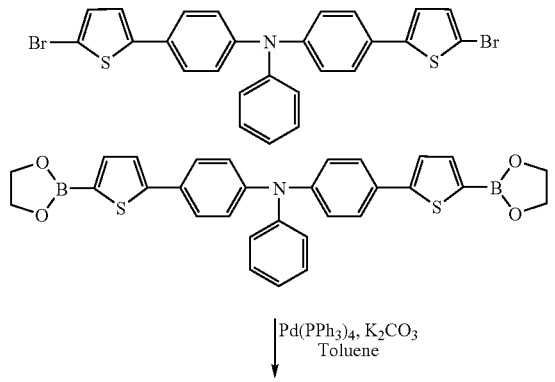

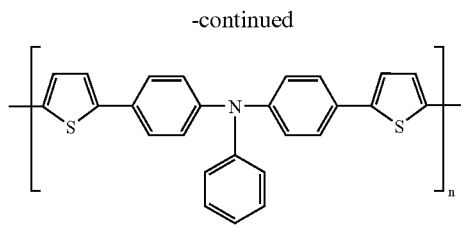

Similarly copolymers according to the invention may be prepared by Yamamoto or Suzuki coupling, Suzuki coupling is preferred. Generally, in order to prepare a copolymer by Suzuki coupling suitably substituted monomers are polymerized in a solvent in the presence of a catalyst. Suitable reactants for the preparation of a two component copolymer are monomers having at least two boronic ester groups and second monomers having at least two Br groups alternatively monomers having one Br group and one boronic ester group and second monomers having one Br group and one boronic ester group. Clearly terpolymers and higher copolymers could be prepared by reacting suitable monomers. The catalyst is a palladium catalyst such as tetrakis(triphenylphosphine)palladium, suitable bases include alkaline earth carbonates and alkaline earth bicarbonates or organic bases such as those disclosed in WO 00/53656. The solvent is preferably one in which the polymer is soluble, for example suitable solvents for polyfluorenes include anisole, benzene, ethylbenzene, mesitylene, xylene and toluene.

End-capping reagents may be added to terminate the reaction or may be added after termination of the reaction. Examples of suitable end-capping reagents include phenylboronate and bromobenzene.

Examples of comonomers which may be copolymerized with the monomers of the present invention to form copolymers include the following, wherein $X_1$ and $X_2$ are polymerizable groups.

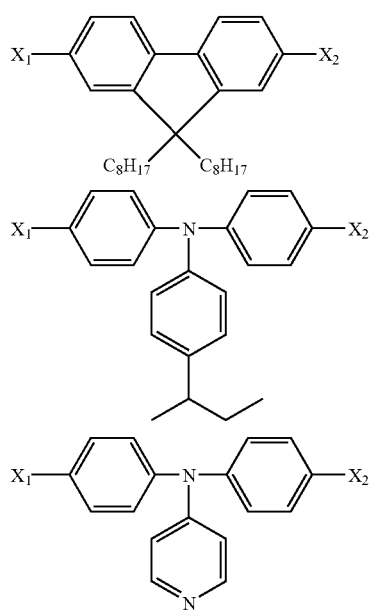

-continued
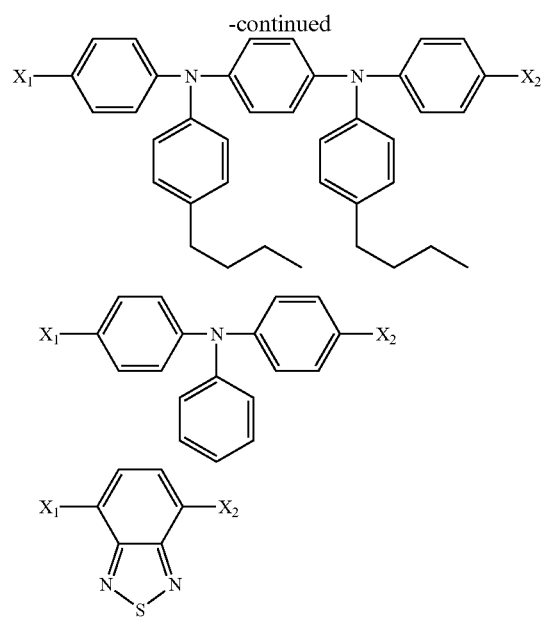
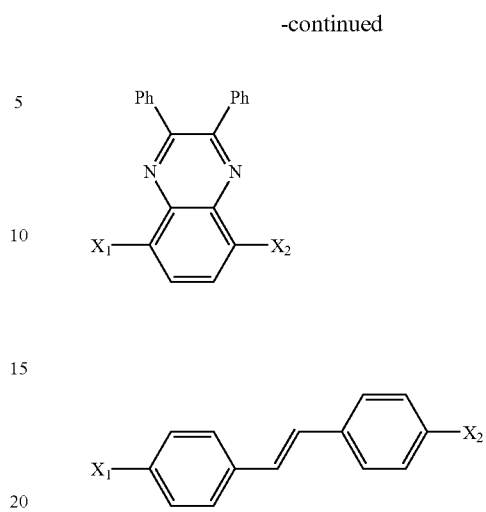
Examples of polymers and copolymers include those having the following structural formulae, wherein x, y and z represent the proportion of monomers in the copolymer.
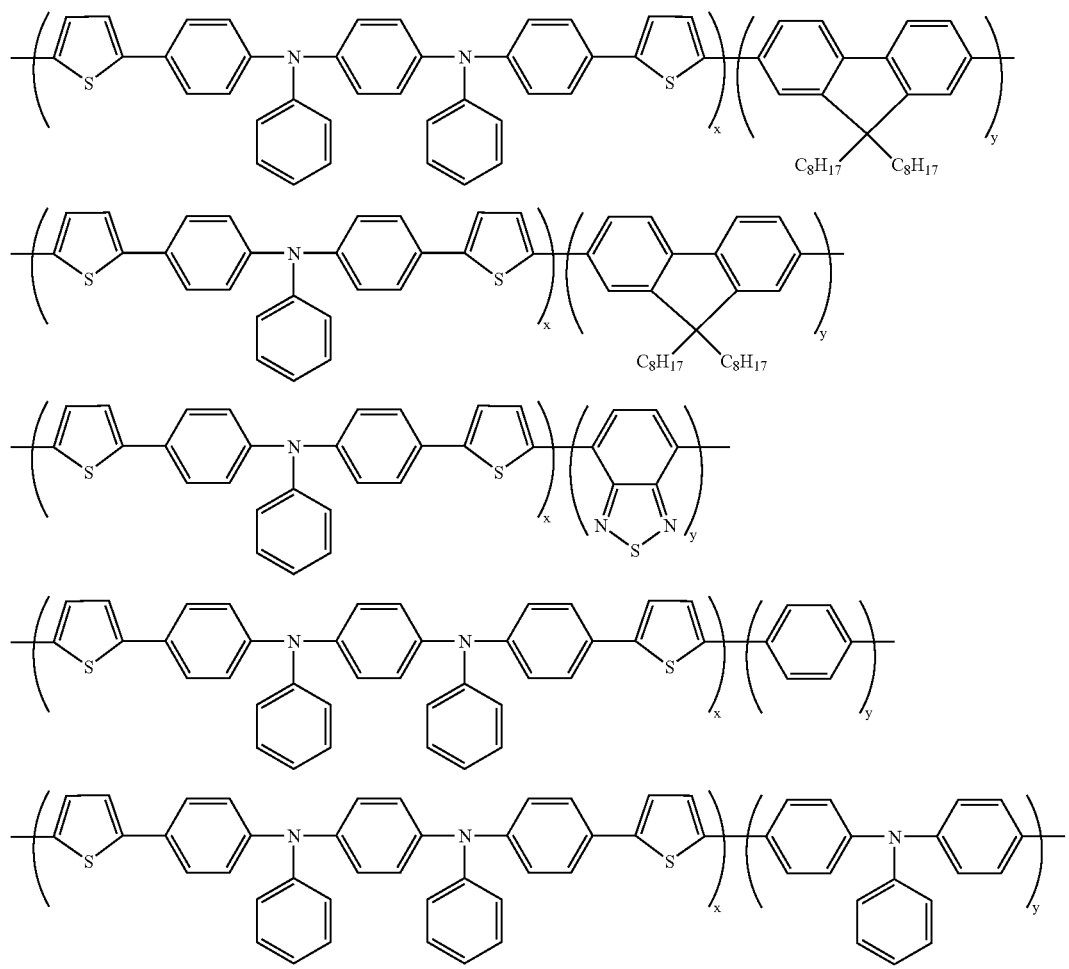

-continued

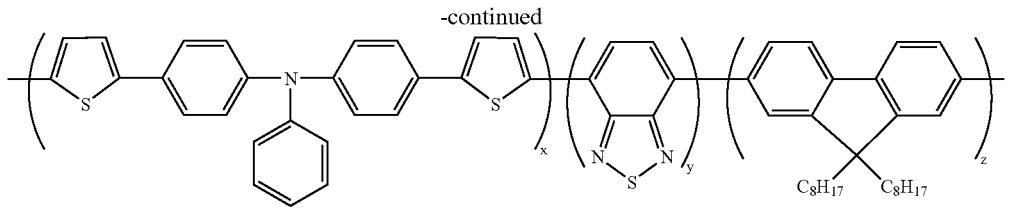

The polymers and copolymers of the invention may be used in optoelectronic devices such as electroluminescent devices and photovoltaic devices. An electroluminescent device according to the invention typically comprises, on a suitable substrate, an anode, a cathode and a layer of light-emitting material positioned between the anode and the cathode. Electroluminescent devices may further comprise charge transport layers and/or charge injecting layers positioned between the light-emitting material and the anode or cathode as appropriate. In electroluminescent devices of the invention the polymers or copolymers of the invention may be present either as the light-emitting layer or as charge transporting or charge injecting layers or alternatively as charge transporting components in a blend with a light emitting material or as light emitting components in a blend with a charge transporting material. The thickness of the emitting layer can be in the range 10 nm-300 nm, preferably 5 nm-200 nm. In particular the polymers and copolymers of the present invention may act as hole-transporting layers or as hole-transporting components in a blend.

The anode of the device preferably comprises a material of high work function deposited on a substrate. Preferably the material has a work function greater than 4.3 eV, examples of such materials include indium-tin oxide (ITO), tin oxide (TO), aluminum or indium doped zinc oxide, magnesium-indium oxide, cadmium tin-oxide and metals such as Au, Ag, Ni, Pd and Pt. Suitable substrates include glass and plastics, the substrate may be rigid or flexible, transparent or opaque. The material of high work function is suitably deposited on the substrate to form a film of 50 nm to 200 nm, preferably said film has a sheet resistance of 10-100 Ohm/square, more preferably less than 30 Ohm/square.

The cathode of the device is preferably a material of low work function, preferably of work function less than 3.5 eV. Examples of such materials include Li, Na, K, Rb, Be, Mg, Ca, Sr, Ba, Yb, Sm and Al. The cathode may comprise an alloy of such metals or an alloy of such metals in combination with other metals, for example the alloys MgAg and LiAl. The cathode preferably comprises multiple layers, for example Ca/Al or LiAl /Al. The device may further comprise a layer of dielectric material between the cathode and the emitting layer, such as is disclosed in WO 97/42666. In particular it is preferred to use an alkali metal or alkaline earth metal fluoride as a dielectric layer between the cathode and the emitting material. A particularly preferred cathode comprises LiF/Ca/Al, with a layer of LiF of thickness from 1 nm to 10 nm, a layer of Ca of thickness of 1 nm to 25 nm and a layer of Al of thickness 10 nm to 500 nm.

Where the electroluminescent device comprises further charge injecting or charge transporting materials, these further materials may be present as separate layers or in a blend with the light emitting material. Examples of suitable charge transporting materials include polystyrene sulfonic acid doped polyethylene dioxythiophene (PEDOT-PSS), polyaniline with anionic dopants such as polymeric anionic dopants, and triarylamines, including polymeric triarylamines such as poly(2,7-(9,9-di-n-octylfluorene)-(1,4-phenylene-(4-imino(benzoic acid))-1,4-phenylene-(4-imino(benzoic acid))-1,4-phenylene))BFA. The charge transport or charge injecting layers suitably have a thickness in the range 10 nm to 200 nm, preferably 1 nm to 50 nm.

A preferred structure of an electroluminescent device comprises a glass substrate, an ITO anode, a charge transporting layer of PEDOT-PSS, a layer of light-emitting material, a thin layer of LiF and a cathode comprising a layer of calcium and a layer of aluminum.

A photovoltaic device according to the invention typically comprises two electrodes and situated between said two electrodes at least two semiconductive polymers having different electron affinities, one of said semiconductive polymers being a polymer according to the present invention. The semiconductive polymers may be in the form of a blend or may form separate layers, preferably said semiconductive polymers are in the form of a blend. Generally one of the electrodes comprises a material of high work function, such as ITO, other examples of suitable high work function materials are given above. Generally the other electrode comprises a material of low work function such as Al, other examples of suitable low work function materials are given above. Photovoltaic devices may comprise further charge injection and/or charge transport layers as appropriate, for example a layer of PEDOT/PSS may be included between the anode and the polymeric layer to aid hole transport and injection. Examples of such photovoltaic devices are disclosed in WO 99/149525 and U.S. Pat. No. 5,670,791.

Polymers according to the invention may also be used as the active component in photodetectors and photoconductors. In a photodetector the polymer is comprised in a layer of organic material situated between two electrodes, a voltage is applied across the layer of organic material and a current detecting circuit is used to measure the current generated due to incident light falling on the organic material. A photoconductor comprising a polymer of the invention operates along similar lines but comprises a circuit to measure the change in resistance across the polymer layer which occurs when the device is exposed to light. Photodiodes and photodetectors are disclosed in WO 99/09603, GB 2,315,594 and U.S. Pat. No. 5,523,555.

EXAMPLES

Synthesis of Trimer Precursor

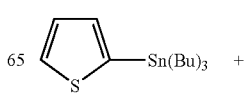

-continued

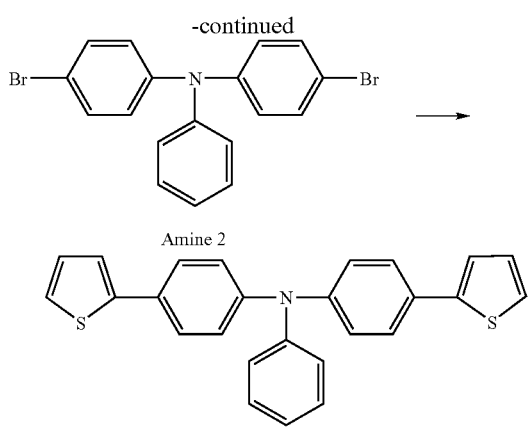

Amine 2

To a solution of 2-tributyl stannyl thiophene (10.16 mL, 17.56 mmol), Amine 2 (7.18 g, 13.3 mmol) in toluene (80 mL) was added tetrakis (triphenylphosphine)palladium(0) (731 mg). The reaction mixture was refluxed for 4 hours and then the heat removed. The suspension was filtered through celite and evaporated to dryness. Recrystallization from hexane afforded 3.98 g (56%yield) of desired product. A further 1.16 g was obtained from the mother liquor. Overall yield (73%). Structure was confirmed by GC-MS and $^1$H NMR.

Synthesis of Dibromo Trimer

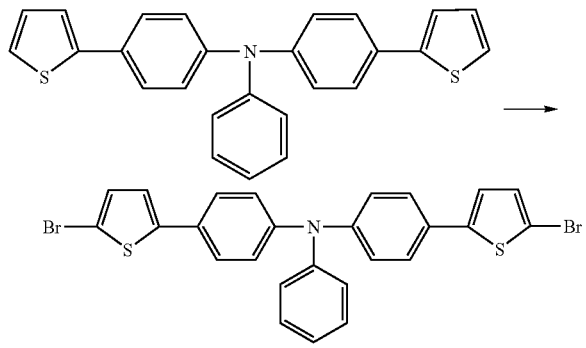

To a solution of trimer precursor (3.97 g, 17.47 mmol) in DMF (40 mL) was added a solution of N—bromo succinimide (NBS) (2.66 g, 14.94 mmol) in DMF (10 mL). The reaction mixture was stirred at room temperature for 30 mins. Monitored by GC-MS. A further 2.66 g of NBS was added, this gave 100% of desired product by GC-MS. The reaction quenched by pouring the reaction mixture onto ice/ethanol. The product was filtered off and recrystallised from diethyl ether/hexane affording, 5.19 g (98% yield) of desired product.

Polymerization of AB copolymer F8Trimer:

To a solution of 9,9-di-n-octylfluorene-2,7-di(ethyleneborate)(F8), (0.9267 g, 1.75 mmol) and dibromo trimer (1.2290 g, 1.75 mmol) in toluene (5 mL) was added dichlorobis(triphenylphosphine)palladium (II) 4 mg in toluene (2.55 mL). The solution was degassed for 10 min then tetraethyl ammonium hydroxide (5.82 mL) was added. The reaction mixture was heated to 115° C. for 19 h. End capping reagents were then added as follows, 0.3 ml bromobenzene was added and allowed to react for 1 hour at a temperature of 115° C., then 0.3 g phenylboronic acid was added and allowed to react for 1 hour at a temperature of 115° C. The reaction mixture was allowed to cool to room temperature and poured into 0.5 l methanol. The polymer was obtained as a precipitate. 1.14 g of polymer of mass 15 K was obtained.

The invention is described with reference to a number of specific embodiments, it will be evident to a person skilled in the art that various modifications may be made within the scope of the invention.

The invention claimed is:

1. Monomer having the formula $$X_1—Ar_1-[triarylamine]-Ar_2—X_2$$

wherein the triarylamine unit comprises at least one nitrogen atom in the backbone of the monomer and at least three substituted or unsubstituted aryl or heteroaryl groups, said groups being the same or different, wherein $X_1$ and $X_2$ are the same or different polymerizable groups, and, wherein $Ar_1$ and $Ar_2$ are the same or different substituted or unsubstituted aryl or heteroaryl groups.

2. Monomer according to claim 1 wherein $Ar_1$ and $Ar_2$ are heteroaryl groups.

3. Monomer according to claim 2 wherein $Ar_1$ and $Ar_2$ are selected from the group consisting of benzene, thiophene, pyrrole, furan, and pyridine.

4. Monomer according to claim 1 wherein $X_1$ and $X_2$ are the same or different and are selected from the group consisting of Cl Br, I, boronic acids, boronic esters, and boranes.

5. Monomer according to claim 4 wherein $X_1$ and $X_2$ are the same or different and are selected from the group consisting of Br and boronic esters.

6. Monomer according to claim 1 wherein the triarylamine group comprises at least one heteroaryl group.

7. Monomer according to claim 6 wherein the triarylamine group comprises a triazine group.

8. Monomer according to claim 1 wherein $Ar_1$ and $Ar_2$ are the same or different aryl or heteroaryl groups and are substituted with moieties selected from the group consisting of alkyl, perfluoroalkyl, alkylaryl, arylalkyl, heteroaryl, aryl, alkoxy, aryloxy, and thioalkyl.

9. Monomer according to claim 1 wherein the triarylamine comprises one nitrogen atom.

10. Monomer according to claim 1 wherein the triarylamine comprises two nitrogen atoms.

11. Monomer according to claim 9 having the structure

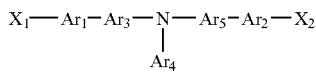

wherein $X_1$ and $X_2$ are the same or different polymerizable groups, and, wherein $Ar_1$, $Ar_2$, $Ar_3$, $Ar_4$ and $Ar_5$ are the same or different substituted or unsubstituted aryl or heteroaryl groups.

12. Monomer according to claim 11 wherein groups $Ar_3$, $Ar_4$, and $Ar_5$ are substituted with moieties selected from the group consisting of alkyl, perfluoroalkyl, alkylaryl, arylalkyl, heteroaryl, aryl, alkoxy, aryloxy, and thioalkyl.

13. Monomer according to claim 10 having the structure

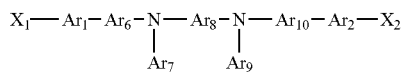

wherein $X_1$ and $X_2$ are the same or different polymerizable groups, and, wherein $Ar_1$, $Ar_2$, $Ar_6$, $Ar_7$, $Ar_8$, $Ar_9$, and $Ar_{10}$ are the same or different substituted or unsubstituted aryl or heteroaryl groups.

14. Monomer according to claim 13 wherein groups $Ar_6$, $Ar_7$, $Ar_8$, $Ar_9$, and $Ar_{10}$ are substituted with moieties selected from the group consisting of alkyl, perfluoroalkyl, alkylaryl, arylalkyl, heteroaryl, aryl, alkoxy, aryloxy, and thioalkyl.

15. Monomers according to claim 1 having the structures

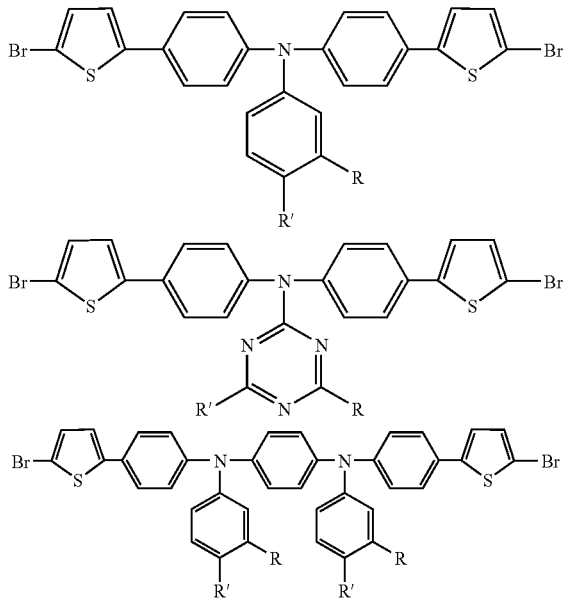

wherein R and R' are selected from the group consisting of alkyl, perfluoroalkyl, alkylaryl, arylalkyl, heteroaryl, aryl, alkoxy, aryloxy, and thioalkyl.

16. Polymer obtained by the polymerization of a monomer according to claim 1.

17. Copolymer obtained by the polymerization of a monomer according to claim 1 and one or more comonomers.

18. Copolymer obtained by the copolymerization of a monomer according to claim 1 and one or more comonomers selected from the group consisting of fluorenes, benzothiadiazoles, phenylenes, triarylamines, stilbenes, quinoxalines, and biphenylenes.

19. Copolymer obtained by the copolymerization of a monomer according to claim 1 and a comonomer selected from the group consisting of fluorenes, benzothiadiazoles, triarylamines, and phenylenes.

20. Optoelectronic device comprising a polymer according to claim 16.

21. Optoelectronic device according to claim 20 wherein said device is an electroluminescent device.

22. Optoelectronic device according to claim 20 wherein said device is a photovoltaic device.

23. A process for preparing a polymer which comprises polymerizing in a reaction mixture (a) a monomer according to claim 1 having at least two boron derivative functional groups selected from the group consisting of boronic acid groups, boronic ester groups, and borane groups, and a monomer according to claim 1 having at least two reactive halide functional groups; or (b) a monomer according to claim 1 having one reactive halide functional group and one boron derivative functional group selected from the group consisting of boronic acid groups, boronic ester groups and borane groups, wherein the reaction mixture comprises a catalytic amount of a catalyst suitable for catalyzing the polymerization of the aromatic monomers, and a base in an amount sufficient to convert the boron derivative functional groups into-$BX_3$-anionic groups, wherein X is independently selected from the group consisting of F and OH.

24. A process for preparing a copolymer, which comprises polymerizing in a reaction mixture (a) a monomer according to claim 1 having at least two boron derivative functional groups selected from the group consisting of boronic acid groups, boronic ester groups and borane groups, and one or more comonomers having at least two reactive halide functional groups; or (b) a monomer according to claim 1 having at least two reactive halide functional groups, and one or more comonomers having at least two boron derivative functional groups selected from the group consisting of boronic acid groups, boronic ester groups, and borane groups; or (c) at least a monomer according to claim 1 having one reactive halide functional group and one boron derivative functional group selected from the group consisting of boronic acid groups, boronic ester groups, and borane groups and one or more comonomers having one reactive halide functional group and one boron derivative functional group selected from boronic acid groups, boronic ester groups and borane groups, wherein the reaction mixture comprises a catalytic amount of a catalyst suitable for catalyzing the polymerization of the aromatic monomers, and a base in an amount sufficient to convert the boron derivative functional groups into-$BX_3$-anionic groups, wherein X is independently selected from the group consisting of F and OH.

25. Optoelectronic device comprising a copolymer according to claim 17.

26. Optoelectronic device according to claim 25 wherein said device is an electroluminescent device.

27. Optoelectronic device according to claim 25 wherein said device is a photovoltaic device.

* * * * *

UNITED STATES PATENT AND TRADEMARK OFFICE
CERTIFICATE OF CORRECTION

PATENT NO.        : 7,348,428 B2
APPLICATION NO.   : 10/493637
DATED             : March 25, 2008
INVENTOR(S)       : O'Dell et al.

Page 1 of 1

It is certified that error appears in the above-identified patent and that said Letters Patent is hereby corrected as shown below:

At Column 15, line 43, "wherein R arid R' are selected" should read as -- wherein R and R' are selected --.

Signed and Sealed this

Thirtieth Day of June, 2009

JOHN DOLL
*Acting Director of the United States Patent and Trademark Office*